(12) United States Patent
Brasch et al.

(10) Patent No.: US 10,365,184 B2
(45) Date of Patent: Jul. 30, 2019

(54) ELECTRICAL DISCHARGE TESTING SYSTEM

(71) Applicant: Paul E. Hawkinson Company, St. Michael, MN (US)

(72) Inventors: Brian B. Brasch, West Fargo, ND (US); Gary William Box, Golden Valley, MN (US)

(73) Assignee: Paul E. Hawkinson Company, Fargo, ND (US)

( * ) Notice: Subject to any disclaimer, the term of this patent is extended or adjusted under 35 U.S.C. 154(b) by 361 days.

(21) Appl. No.: 15/198,243

(22) Filed: Jun. 30, 2016

(65) Prior Publication Data
US 2017/0003240 A1 Jan. 5, 2017

Related U.S. Application Data

(60) Provisional application No. 62/186,723, filed on Jun. 30, 2015.

(51) Int. Cl.
*G01R 27/20* (2006.01)
*G01M 17/02* (2006.01)
*G01N 27/60* (2006.01)

(52) U.S. Cl.
CPC .......... *G01M 17/021* (2013.01); *G01N 27/60* (2013.01)

(58) Field of Classification Search
CPC ............................ G01M 17/021; G01N 27/60
USPC ........................................................ 324/558
See application file for complete search history.

(56) References Cited

U.S. PATENT DOCUMENTS

| 4,297,876 A | 11/1981 | Weiss |
| 4,327,579 A | 5/1982 | Weiss |
| 4,365,514 A | 12/1982 | Ho |
| 4,372,366 A | 2/1983 | Dugger |
| 4,516,068 A | 5/1985 | Hawkinson, Jr. |
| 4,520,307 A | 5/1985 | Weiss |
| 4,936,138 A | 6/1990 | Cushman |
| 4,949,030 A * | 8/1990 | Tse ........................ H02M 3/335 324/118 |
| 5,276,301 A * | 1/1994 | Kohsaka .................. B23H 7/04 219/69.12 |
| 5,531,109 A | 7/1996 | Tsagas |
| 6,050,136 A | 4/2000 | Hawkinson |
| 6,269,689 B1 | 8/2001 | Alexander |
| 6,304,090 B1 | 10/2001 | Weiss |
| 6,600,326 B2 | 7/2003 | Weiss |
| 6,832,513 B2 | 12/2004 | Weiss |

(Continued)

*Primary Examiner* — Melissa J Koval
*Assistant Examiner* — Courtney G McDonnough
(74) *Attorney, Agent, or Firm* — Neustel Law Offices

(57) ABSTRACT

An electrical discharge testing system for detecting electrical discharge rate failure in an electrical-based tire defect tester. The electrical discharge testing system generally includes a probe which is connected to a power source such that the probe periodically discharges electricity for the purpose of testing a tire for defects. A sensor detects each electrical discharge of the probe. To ensure that the probe is discharging at an appropriate rate for efficient coverage of the tire, a timer is preset to a threshold period of time between electrical discharges. The timer is reset each time an electrical discharge from the probe is detected by the sensor. If the timer reaches zero before a subsequent electrical discharge after a reset, an indicator is activated to indicate a fault in the tire defect tester.

15 Claims, 14 Drawing Sheets

(56) References Cited

U.S. PATENT DOCUMENTS

| | | |
|---|---|---|
| 6,837,102 B2 | 1/2005 | Weiss |
| 6,907,777 B2 | 6/2005 | Weiss |
| 7,021,132 B2 | 4/2006 | Nigon |
| 7,096,727 B2 | 8/2006 | Adamson |
| 7,302,836 B2 | 12/2007 | Hattori |
| 7,439,928 B2 | 10/2008 | Forster |
| 7,882,742 B1 | 2/2011 | Martens |
| 8,291,753 B2 | 10/2012 | Range |
| 8,733,160 B2 | 5/2014 | Range |
| 9,222,853 B2 | 12/2015 | Range |
| 2002/0011849 A1 | 1/2002 | Weiss |
| 2005/0134444 A1 | 6/2005 | Park |
| 2006/0050447 A1* | 3/2006 | Pellon .................. H02H 1/0015 361/5 |
| 2013/0139581 A1* | 6/2013 | Range ..................... G01M 3/40 73/146 |

\* cited by examiner

ELECTRICAL DISCHARGE TESTING SYSTEM

CROSS REFERENCE TO RELATED APPLICATIONS

I hereby claim benefit under Title 35, United States Code, Section 119(e) of U.S. provisional patent application Ser. No. 62/186,723 filed Jun. 30, 2015. The 62/186,723 application. The 62/186,723 application is hereby incorporated by reference into this application.

STATEMENT REGARDING FEDERALLY SPONSORED RESEARCH OR DEVELOPMENT

Not applicable to this application.

BACKGROUND

Field

Example embodiments in general relate to an electrical discharge testing system for detecting electrical discharge rate failure in an electrical-based tire defect tester.

Related Art

Any discussion of the related art throughout the specification should in no way be considered as an admission that such related art is widely known or forms part of common general knowledge in the field.

Throughout the decades of car travel, there have been many new methods and systems for detecting defects quickly and efficiently in a tire. Common systems include the use of a pool of liquid such as water into which the tire may be submerged so that bubbles streaming from holes in the tire may be detected. More modern tire defect detectors have been created which utilize electrical discharges to detect defects in tires.

Such electrical-based tire defect detectors typically use a pair of electrodes which are positioned on either side of a tire to be tested. The tire is rotated while one of the electrodes periodically discharges from a connected power supply such as by using a capacitor and a rectifier. Arcs or sparks between the two electrodes will provide an indication that there is a defect at the position in which the arc or spark occurred. Numerous previous patents covering such tire defect testers are disclosed and incorporated by reference herein.

While these electrical-based tire defect testers have provided clear improvements in the art, they still suffer from defects. Perhaps the most common defect in such tire defect testers is wear on the electrodes in the power supply for such testers. As the electrodes wear from repeated arcing, the spacing between the electrodes increases. With a greater distance between the electrodes, a greater charge is necessary by the power supply before the electrical discharge will be generated at the probe. With greater charge comes a great duration of time between discharges. If the probe is not optimized on rate of discharge, it cannot be guaranteed that all surfaces of the tire being tested are being covered, and defects may be missed.

SUMMARY

An example embodiment of the present invention is directed to an electrical discharge testing system. The electrical discharge testing system includes a probe which is connected to a power source such that the probe periodically discharges electricity for the purpose of testing a tire for defects. A sensor detects each electrical discharge of the probe. To ensure that the probe is discharging at an appropriate rate for efficient coverage of the tire, a timer is preset to a threshold period of time between electrical discharges. The timer is reset each time an electrical discharge from the probe is detected by the sensor. If the timer reaches zero before a subsequent electrical discharge after a reset, an indicator is activated to indicate a fault in the tire defect tester.

There has thus been outlined, rather broadly, some of the features of the electrical discharge testing system in order that the detailed description thereof may be better understood, and in order that the present contribution to the art may be better appreciated. There are additional features of the electrical discharge testing system that will be described hereinafter and that will form the subject matter of the claims appended hereto. In this respect, before explaining at least one embodiment of the electrical discharge testing system in detail, it is to be understood that the electrical discharge testing system is not limited in its application to the details of construction or to the arrangements of the components set forth in the following description or illustrated in the drawings. The electrical discharge testing system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
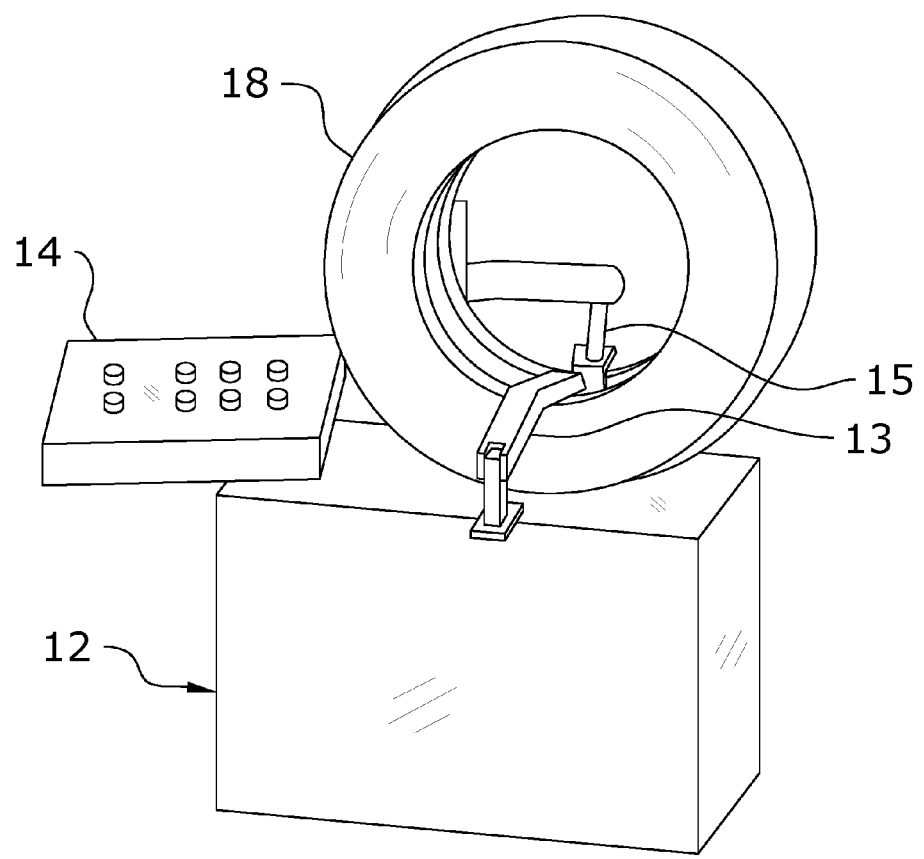
FIG. 1 is a perspective view of an exemplary tire defect tester.

A. Overview.

An example electrical discharge testing system generally comprises a system and method for detecting electrical discharge rate failures in electrical tire defect testers 12. A probe 30 is connected to a power source 32 such that the probe 30 periodically discharges electricity for the purpose of testing a tire 18 for defects 19. A sensor 50 detects each electrical discharge of the probe 30. To ensure that the probe 30 is discharging at an appropriate rate for efficient coverage of the tire 18, a timer is preset to a threshold period of time between electrical discharges. The timer is reset each time an electrical discharge from the probe 30 is detected by the sensor 50. If the timer reaches zero before a subsequent electrical discharge after a reset, an indicator 70 is activated to indicate a fault in the tire defect tester 12.

B. Tire Defect Testers.

Figure 2:
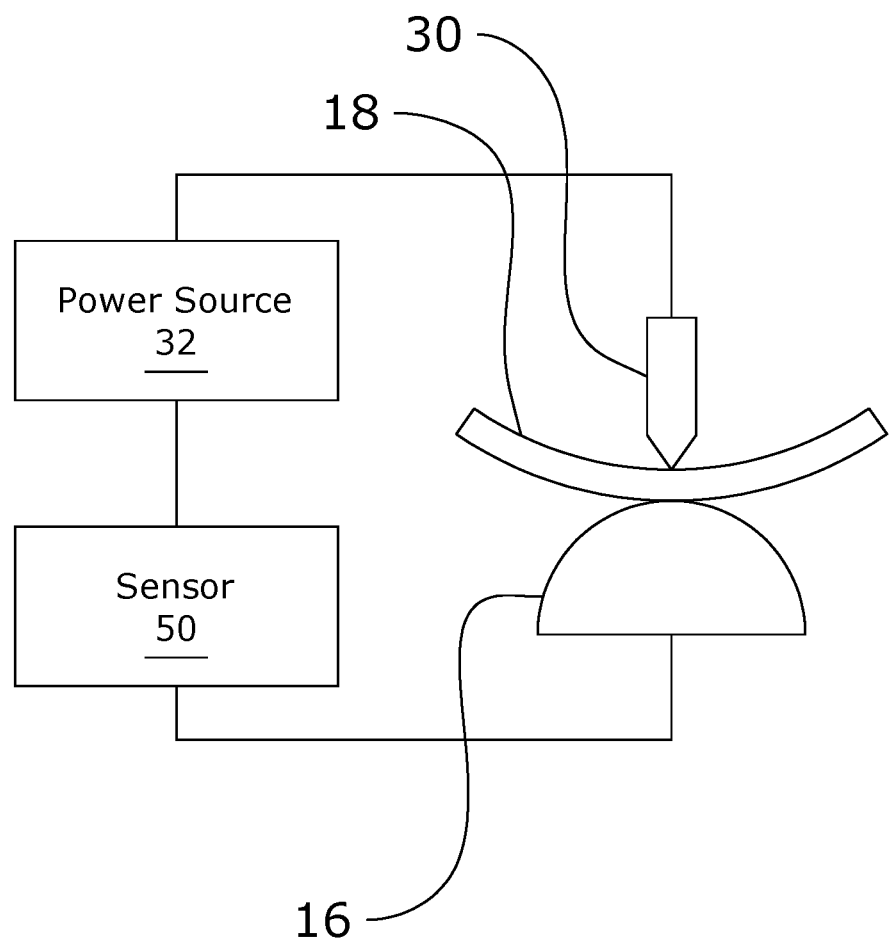
FIG. 2 is a block diagram illustrating an exemplary tire defect tester testing for defect in a tire.
Figure 3:
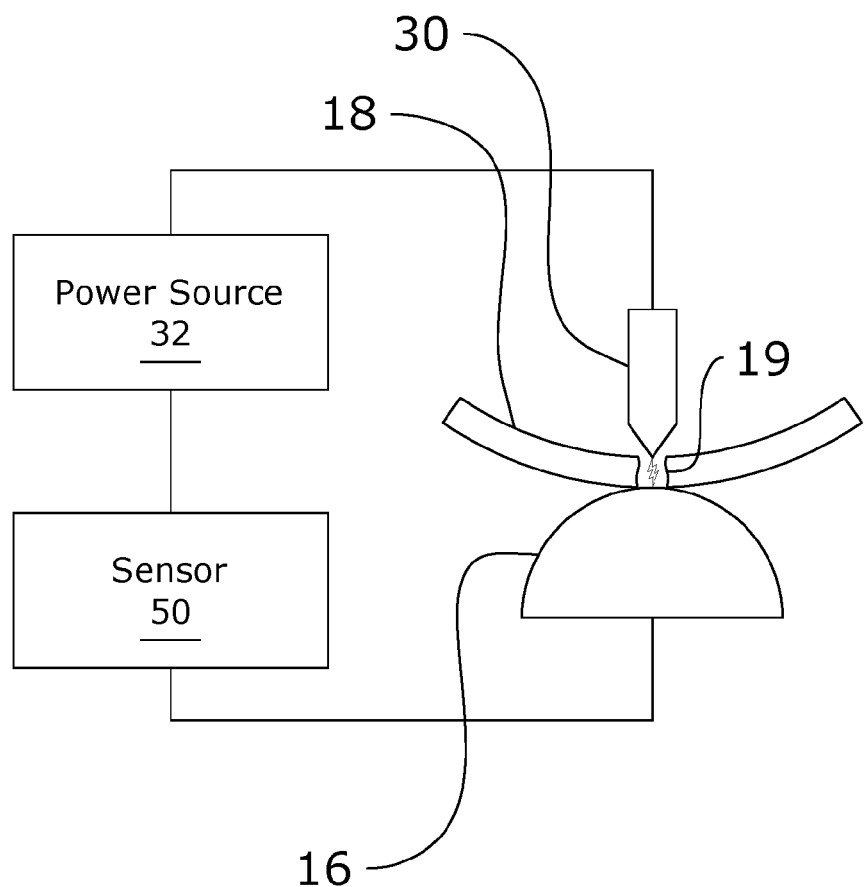
FIG. 3 is a block diagram illustrating an exemplary tire defect tester finding a defect in a tire.

The methods and systems described herein relate to fault detection of electrical tire defect testers 12. An exemplary tire defect tester 12 is shown in FIGS. 1-3. It should be appreciated that the tire defect tester 12 shown in the figures is merely for illustrative purposes only, and thus the present invention should not be construed as limited in any way to a particular type of electrical tire defect tester 12. The methods and systems described herein could be utilized with any type of tire defect tester 12 which utilizes periodic electrical discharges to test for tire defects 19 in a tire 18.

As shown in FIG. 1, an exemplary tire defect tester 12 is adapted to removably receive a tire 18 for testing. The tire 18 is positioned on the tire defect tester 12 and spread by tire spreaders 13. A probing assembly 15 including a probe 30 is then inserted against a first surface of the tire 18, with a grounded roller 16 positioned opposite the probe 30 against a second surface of the tire 18 as shown in FIG. 2. The tire 18 is then rotated along the grounded roller 16 with the probe 30 periodically electrically discharging. A control panel 14 may be provided with the tire defect tester 12 for controlling its various functionality.

The probe 30 periodically discharges an electrical pulse toward the grounded roller 16 through the tire 18. Tire defects 19 in the tire 18 will cause arcs or other changes which can be detected in various manners to locate the tire defects 19 for repair. FIG. 3 illustrates an exemplary tire defect 19 causing an electrical arc between the probe 30 and the grounded roller 16.

It is important that the probe 30 discharge at a rate which allows for full coverage of the tire 18. If the probe 30 discharges too quickly or too slowly, parts of the tire 18 may not be covered by the electrical discharges and thus tire defects 19 could be missed. The optimal electrical discharge rate of the probe 30 will vary for different tire defect testers 12 depending on the type of tires 18 being tested and the rotation speed of the tire defect tester 12. It is preferable that the systems and methods described herein allow for the threshold rate of electrical discharge by the probe 30 to be manually adjusted to accommodate different applications.

An example tire defect tester 12 which would benefit from use of the systems and methods described herein is U.S. Pat. No. 9,222,853, entitled "Tire Defect Tester Having a Fault Indicator Circuit" and filed on May 27, 2014, which is hereby incorporated by reference for all purposes. An additional example tire defect tester 12 is shown in U.S. Pat. No. 8,733,160, entitled "Tire Defect Tester" and filed on Sep. 25, 2012, which is hereby incorporated by reference for all purposes. An additional example tire defect tester 12 is shown in U.S. Pat. No. 8,291,753, entitled "Tire Defect Tester" and filed on May 29, 2008, which is hereby incorporated by reference for all purposes. An additional example tire defect tester 12 is shown in U.S. Pat. No. 6,050,136, entitled "Tire Defect Detection Employing Electrical Arcing" and filed on Apr. 16, 1998, which is hereby incorporated by reference for all purposes. An additional example tire defect tester 12 is shown in U.S. Pat. No. 4,520,307, entitled "High-Voltage Tire Testing Apparatus" and filed on Mar. 8, 1984, which is hereby incorporated by reference for all purposes. An additional example tire defect tester 12 is shown in U.S. Pat. No. 4,516,068, entitled "Tire Defect Tester" and filed on Apr. 16, 1982, which is hereby incorporated by reference for all purposes.

C. Probe and Power Source.

Most tire defect testers 12 which may benefit from the methods and systems described herein will comprise a probe 30 which periodically discharges electricity toward an electrode such as a grounded roller 16 as shown in FIG. 3. The probe 30 is adapted to periodically electrically discharge to test for tire defects 19 in a tire 18. The manner in which the probe 30 pulses electrical discharges, and the manner in which power is supplied to the probe 30, may vary in different embodiments.

In the exemplary embodiments shown in the figures, the probe 30 is connected to a power source 32 such as a high voltage AC input via a current transformer 20. More specifically, a high voltage pulse source 32 is connected through a primary coil 22 of the transformer 20 to the probe 30 such as shown in FIGS. 4 and 5. Various types of transformers 20 may be utilized with varying turn ratios. By way of example and without limitation, a transformer 20 may be utilized with a turn ratio of approximately 121:1 in some embodiments to create a high voltage pulse for the electrical discharge of the probe 30.

The power source 32 will send power through the primary coil 22 of the transformer 20 before it reaches the probe 30 to be discharged. Each time the power source 32 provides a pulse through the primary coil 22 of the transformer 20 to the probe 30, a current pulse is created through the secondary coil 24 of the transformer 20. This current pulse may be detected by the sensor 50 to determine a period of time between electrical discharges of the probe 30.

Figure 4A:
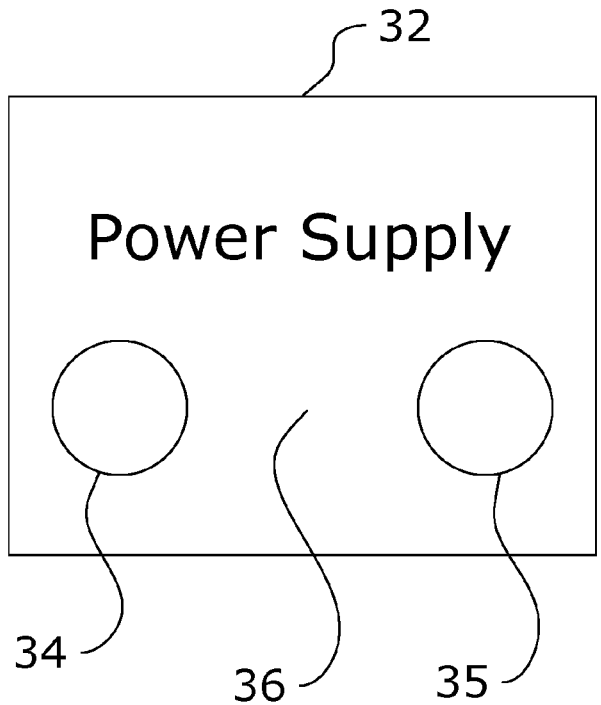
FIG. 4a is a block diagram illustrating an exemplary power supply used with a tire defect tester.
Figure 4B:
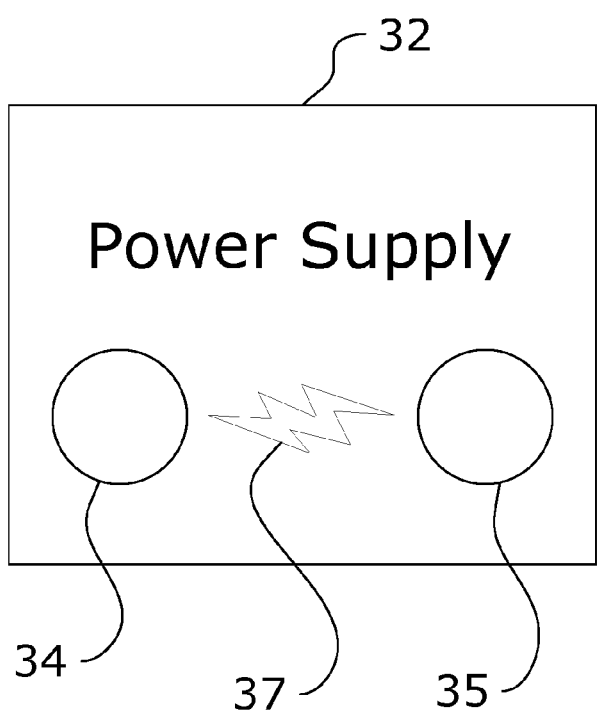
FIG. 4b is a block diagram illustrating an exemplary power supply use with a tire defect tester at the time of a pulse being discharged.
Figure 5:
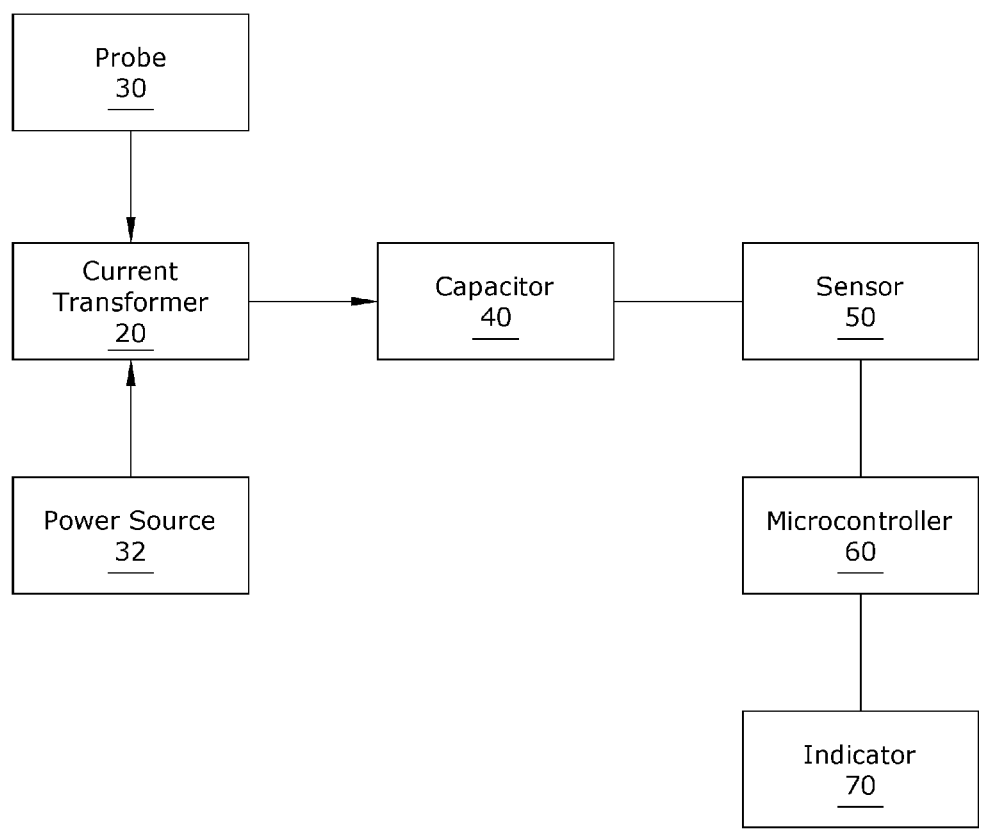
FIG. 5 is a block diagram illustrating an exemplary embodiment of an electrical discharge testing system.

FIGS. 4a and 4b illustrate an exemplary power source 32 which is used with an exemplary tire defect tester 12. The exemplary power source 32 includes a first electrode 34 and a second electrode 35 which are separated by a spark gap 36. A network of resistors and capacitors will result in the periodic discharge of a spark 37 across the spark gap 36 when a certain voltage across the spark gap 36 is reached (for example, 50 KV). This discharge across the electrodes 34, 35 is necessary for each discharge of the probe 30.

A more detailed explanation of such a power source 32, which is commonly used in tire defect testers 12, can be found in U.S. Pat. No. 8,291,753, entitled "Tire Defect Tester" and filed on May 29, 2008; with specifics being described in Columns 10 and 11 and shown in FIG. 8 thereof. This reference has been previously incorporated by reference. It should be appreciated that various other types of power sources 32 may be utilized in different embodiments, and this is merely an illustrative example.

Figure 8:
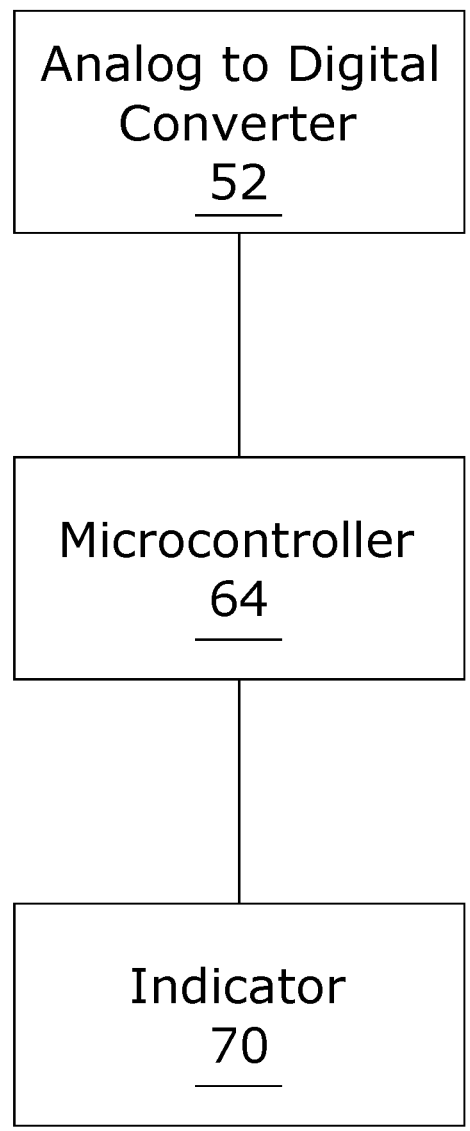
FIG. 8 is a block diagram illustrating an exemplary embodiment in which an analog-to-digital converter and microcontroller are used with the electrical discharge testing system.
Figure 9:
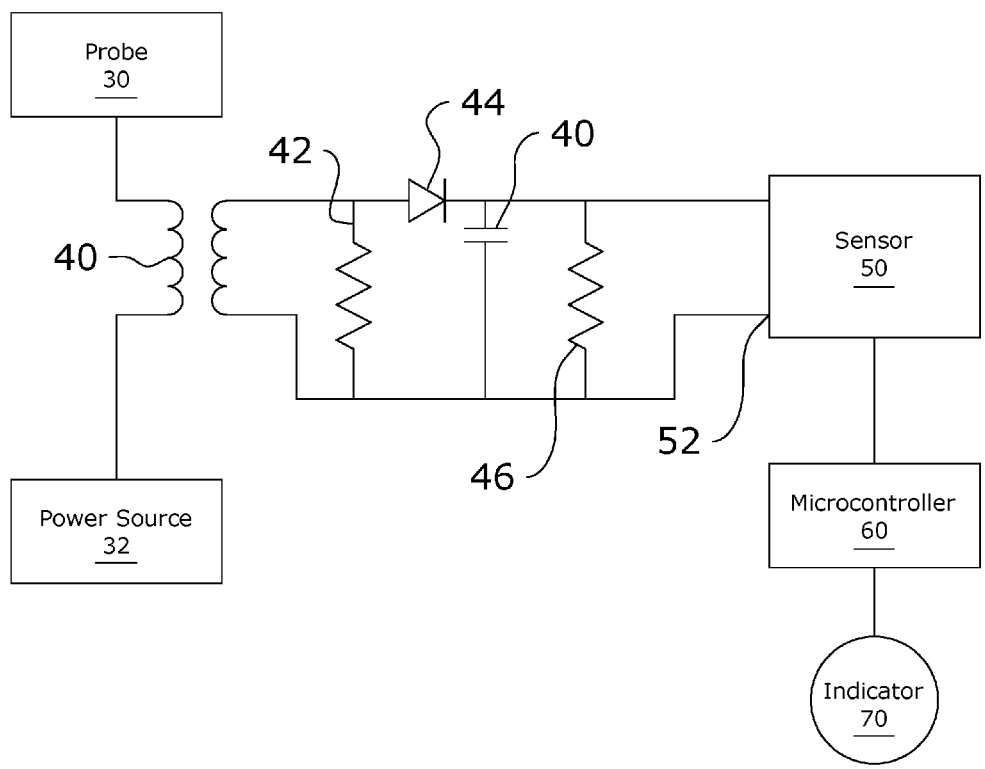
FIG. 9 is a block and circuit diagram illustrating an exemplary embodiment of an electrical discharge testing system.

When using such power sources 32 in a tire defect tester 12, it is common that, with repeated uses, the electrodes 34, 35 may become worn. The electrodes 34, 35 will generally comprise spherical balls of carbon or other materials such as shown in FIG. 8 of the '753 patent. These balls will become worn with repeated usage due to the high voltage arcing across the spark gap 36.

With wear, the distance between the electrodes 34, 35, and thus the size of the spark gap 36, increases. With increased space between the electrodes 34, 35, the charge necessary by the power supply 32 to feed an electrical discharge of the probe 30 will be increased. This necessary added charge which is caused by increased spacing between the electrodes 34, 35 will increase the period of time between electrical discharges of the probe 30. If the probe 30 does not discharge at an optimal rate, such as by discharging at a slower rate than optimal, the probe 30 may not discharge over the entire surface of the tire 18 and tire defects 19 may be missed.

The secondary coil 24 of the transformer 20 will preferably be electrically interconnected with a capacitor 40 as shown in FIG. 5 such that the capacitor 40 charges whenever the probe 30 electrically discharges. More specifically, each current pulse in the secondary coil 24 will preferably charge the capacitor 40. In some embodiments, the sensor 50 may be connected to the probe 30. The subsequent discharge of the capacitor 40 may be sensed by the sensor 50 to determine timing between electrical discharges of the probe 30.

The transformer 20 may be interconnected with the capacitor 40 via various methods. In an embodiment shown in FIGS. 5 and 8, the secondary coil 24 of the transformer 20 is connected to the capacitor 40 via a burden resistor 42 and a diode 44. The current pulse through the secondary coil 24 of the transformer 20 will produce a voltage across the burden resistor 42 and thus charge the capacitor 40 through the diode 44. Various other methods and configurations may be utilized, however, so long as the electrical discharge of the probe 30 results in a corresponding charge of the capacitor 40 via the transformer 20.

In the embodiment shown in FIGS. 5 and 8, the discharge of the capacitor 40 is connected in parallel with a bleed resistor 46. Each time the capacitor 40 is charged via the secondary coil 24 of the transformer 20, the charge of the capacitor 40 is dissipated through the bleed resistor 46. This discharge and dissipation produces a triangular-shaped voltage which may be utilized by the sensor 50 to determine when a first discharge ends and a second discharge begins. Using this information, the period of time between discharges may be calculated to determine whether the discharges are not optimally timed for detection of tire defects 19 in a tire 18 by a tire defect tester 12.

The bleed resistor 46 is preferably connected to the input of a sensor 50 such as an analog-to-digital converter 52, comparator 62, and/or microcontroller 60. In some embodiments, the bleed resistor 46 may be omitted so long as the capacitor 40 is configured to charge and discharge when the probe 30 electrically discharges and the sensor 50 is configured to detect the discharge of the capacitor 40.

D. Sensor and Microcontroller.

Various types of sensors 50 may be utilized to detect electrical discharges of the probe 30. The sensor 50 will generally be adapted to detect when a period of time between discharges of the probe 30 exceeds a threshold. The sensor 50 may be adapted to detect each discharge of the capacitor 40 to determine the period of time between discharges of the probe 30.

Different sensor 50 embodiments are shown in FIGS. 5-9. Generally, as shown in FIG. 5 the sensor 50 will be interconnected or integral with a microcontroller 60 which performs the various functions such as timing and the like of the present invention. The microcontroller 60 is preferably configured to calculate the period of time between detected electrical discharges of the probe 30. Various types of microcontrollers 60 may be utilized; with some embodiments utilizing a microcontroller 60 which also functions as a sensor 50. In other embodiments, the sensor 50 and microcontroller 60 may be separate.

Figure 6:
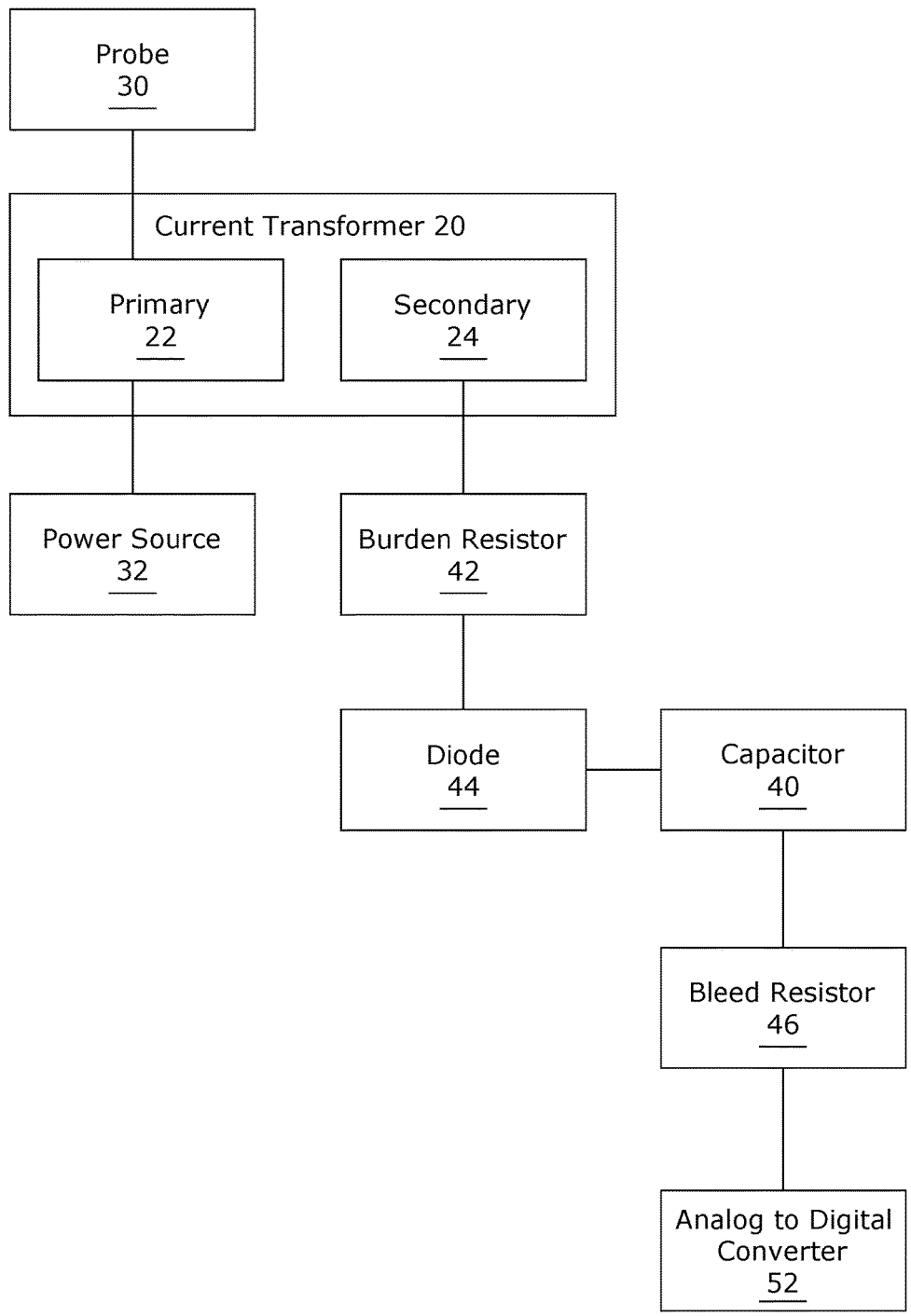
FIG. 6 is a block diagram illustrating exemplary electrical components of an exemplary embodiment of an electrical discharge testing system.

FIGS. 6 and 8 illustrate an embodiment in which an analog-to-digital converter 52 is utilized in combination with the microcontroller 60 and the capacitor 40 to provide sensing of electrical discharges by the probe 30. In such an embodiment, the bleed resister 46 or the discharge of the capacitor 40 may be connected to the input of the analog-to-digital converter 52.

The analog-to-digital converter 52 may or may not be integrated with the microcontroller 60. In either case, the microcontroller 60 will continuously sample the analog-to-digital converter at a sampling rate which is preferably significantly faster than the discharge rate of the capacitor 40. By comparing each analog-to-digital conversion value to the previous value, the microcontroller 60 may detect the rising edge of the triangular voltage waveform on the capacitor 40.

At each rising edge, the microcontroller 60 may check the value of an internal countdown timer that was reset to a value representing the minimum allowable electrical discharge pulse width at the previous rising edge. If this timer value is zero, the electrical discharge rate of the probe 30 has fallen below the rate threshold and the microcontroller 60 will thus find a fault in the tire defect tester 12. If the timer value is not zero, the electrical discharge rate of the probe 30 has not fallen below the rate threshold and the microcontroller 60 will not find a fault in the tire defect tester 12 and will thus continue with normal operation.

Figure 7:
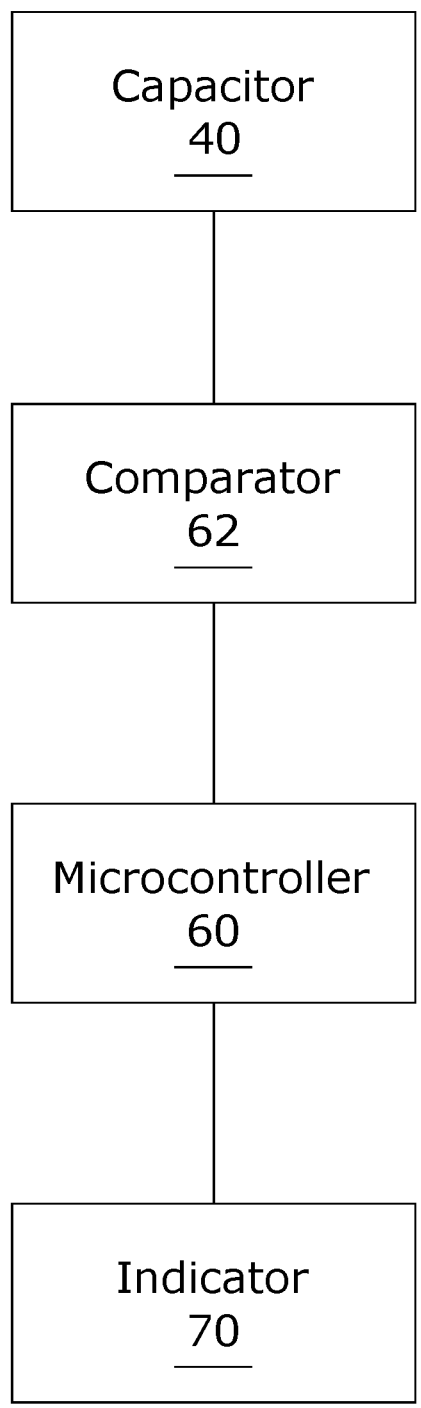
FIG. 7 is a block diagram illustrating an exemplary embodiment in which a comparator and microcontroller are used with the electrical discharge testing system.

FIG. 7 illustrates an alternate embodiment utilizes a comparator 62 in place of the analog-to-digital converter 52. The comparator 62 may be set to a fixed value to represent the threshold for an optimal electrical discharge rate of the probe 30. The output of the comparator 62 may be connected to the microcontroller 60, though in some embodiments the comparator 62 may be integrated directly with the microcontroller 60.

In either case, the leading edge of the signal coming from the comparator 62 may be utilized by the microcontroller 60 to test and reset a countdown timer. More specifically, the microcontroller 60 may recognize and use the leading edge of the signal to determine a period of time between electrical discharges of the probe 30. This period of time may be compared with the optimal period of time to determine whether a fault is occurring in the electrical discharge rate of the probe 30.

E. Indicator.

An indicator 70 is preferably provided to provide an indication of when a defect or fault has been detected in the electrical discharge rate of the probe 30 of a tire defect tester 12. More specifically, the indicator 70 may be adapted to provide an indication when the period of time between discharges of the probe 30 exceeds a threshold.

The indicator 70 may be integrated with the tire defect tester 12 or may be on a discrete device. In some embodiments, the indicator 70 may be a remote device which is communicatively interconnected with the microcontroller 60, such as via a communications network. In other embodiments, the indicator 70 may be hardwired to the microcontroller 60.

The indicator 70 may comprise any device or method which would alert an operator of the tire defect tester 12 that the electrical discharge rate of the probe 30 is suboptimal. By way of example and without limitation, the indicator 70 could comprise a blinking light, a light that turns on or off, an audible alarm, or various other alerts, alarms, and the like which would be noticeable to an operator of a tire defect tester 12.

In some embodiments, the tire defect tester 12 may automatically shut-off if a fault is detected. In other embodiments, the tire defect tester 12 may be configured to send out an alert via a communications network, such as an email, SMS text message, or the like, to a third-party device which itself will provide the alert or alarm to the operator.

F. Operation of Preferred Embodiment.

Figure 10:
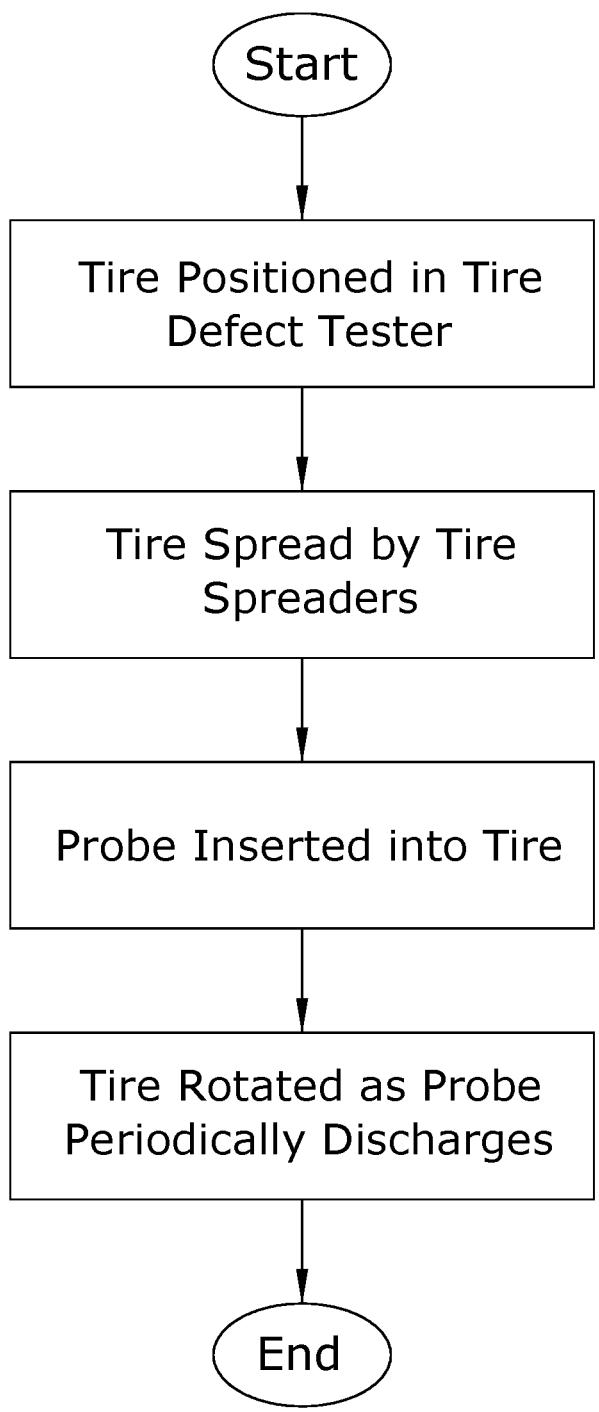
FIG. 10 is a flowchart illustrating an exemplary method of testing a tire for defects.

FIGS. 10-14 are flowcharts illustrating exemplary methods for detecting an electrical discharge fault in a tire defect tester 12. FIG. 10 illustrates an exemplary operation of a tire defect tester 12. As shown, the tire 18 is first positioned on the tire defect tester 12 such as shown in FIG. 1. Tire spreaders 13 may be utilized to pull the tire 18 open so that a probing assembly 15 including the probe 30 may be lowered into the tire 18. The tire 18 is then rotated along a grounded roller 16 such that electrical discharges from the probe 30 are directed through the tire 18 at the grounded roller 16. When a defect is detected, an arc or spark will extend between the probe 30 and the grounded roller 16 as shown in FIG. 3.

It is important that the probe 30 electrically discharge at a sufficient rate to allow for full coverage of the tire 18 by the electrical discharges. If the probe 30 discharges too slowly, areas of the tire 18 will be missed and tire defects 19 may not be detected, thus compromising the functionality of the entire tire defect tester 12. The methods and systems described herein are directed toward detecting such faults in the rate of discharge of the probe 30 to prevent tire defects 19 from being missed.

Broadly speaking, an exemplary embodiment functions by periodically discharging the probe 30 to test for tire defects 19 in the tire 18. An optimal period of time between electrical discharges of the probe 30 may be preset in the microcontroller 60. The optimal period of time between electrical discharges of the probe 30 will vary for different types of tire defect testers 12 and different types of tires 18. The optimal period of time may be represented by the minimum amount of time between electrical discharges of the probe 30 which will allow for the electrical discharges to fully cover the surface of the tire 18 to search for tire defects 19.

Figure 12:
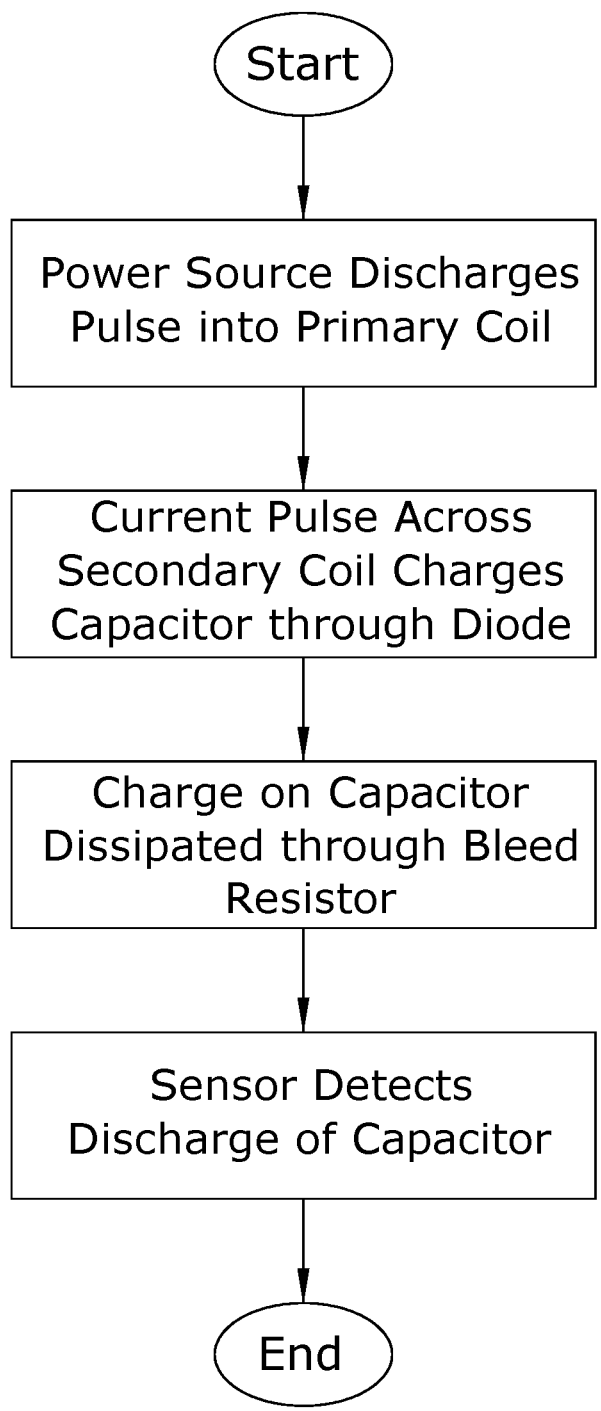
FIG. 12 is a flowchart illustrating an exemplary method for sensing electrical discharges in a tire defect tester.

The sensor 50 will function by detecting each electrical discharge of the probe 30 such as in the manner shown in FIG. 12. By way of example, the sensor 50 may detect a first electrical discharge from the probe 30. For example, a first current pulse is created across the secondary coil 24 of the transformer 20 upon the first electrical discharge from the probe 30. The sensor 50 may detect the first current pulse to indicate that the first electrical discharge from the probe 30 has occurred.

The sensor 50 will then detect the subsequent second electrical discharge from the probe 30. For example, a second current pulse is created across the secondary coil 24 of the transformer 40 upon the second electrical discharge from the probe 30. The sensor 50 may detect the second current pulse to indicate that the second electrical discharge from the probe 30 has occurred. By calculating a period of time between the first electrical discharge of the probe 30 and the second electrical discharge of the probe 30, the microcontroller 60 may determine if a fault is occurring in the electrical discharge rate of the probe 30.

The microcontroller 60 will generally indicate a fault if the period of time between the first electrical discharge of the probe 30 and the second electrical discharge of the probe 30 exceeds the optimal period of time which was preset. The microcontroller 60 will not indicate a fault if the period of time between the first electrical discharge of the probe 30 and the second electrical discharge of the probe 30 is equal to or less than the optimal period of time.

Figure 11:
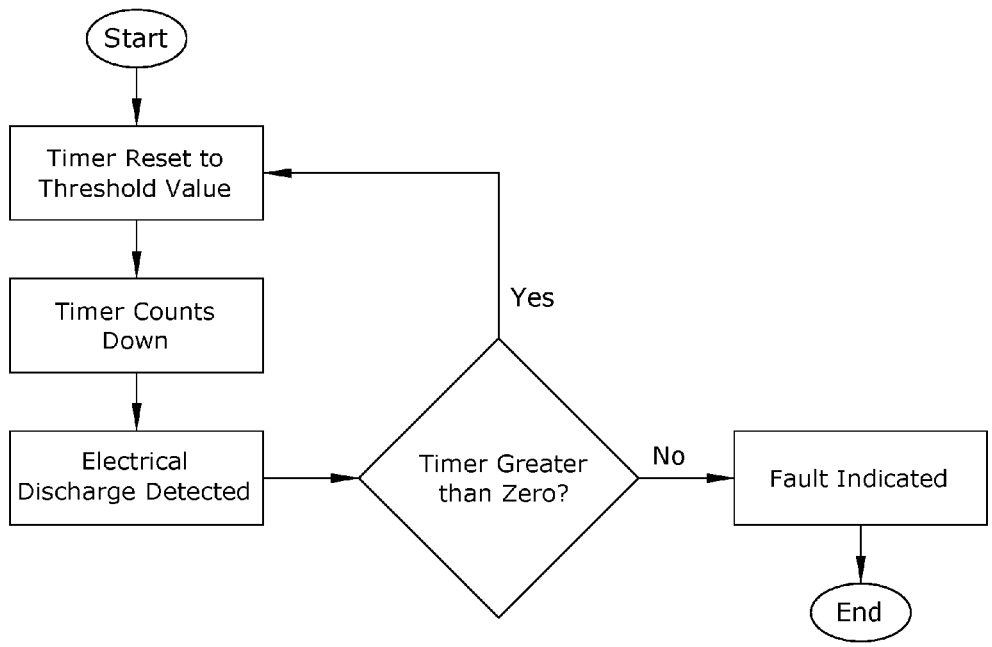
FIG. 11 is a flowchart illustrating an exemplary method for determining whether a fault is present in the electrical discharge of a tire defect tester.

The manner by which the microcontroller 60 calculates the period of time may vary in different embodiments. In one embodiment such as shown in FIG. 11, the microcontroller 60 will reset a countdown timer each time an electrical discharge from the probe 30 is sensed by the sensor 50. The countdown timer will relate to the minimum period of time between electrical discharges for optimal performance.

Upon detection of a subsequent electrical discharge from the probe 30 by the sensor 50, the microcontroller 60 will check whether the timer is zero. If the timer is zero, the time between pulses exceeds the optimal time and a fault may be indicated. If the timer is above zero, the time between pulses does not exceed the optimal time and a fault is not indicated. The timer is then reset by the microcontroller and starts counting down for the subsequent electrical discharge of the probe 30.

Figure 13:
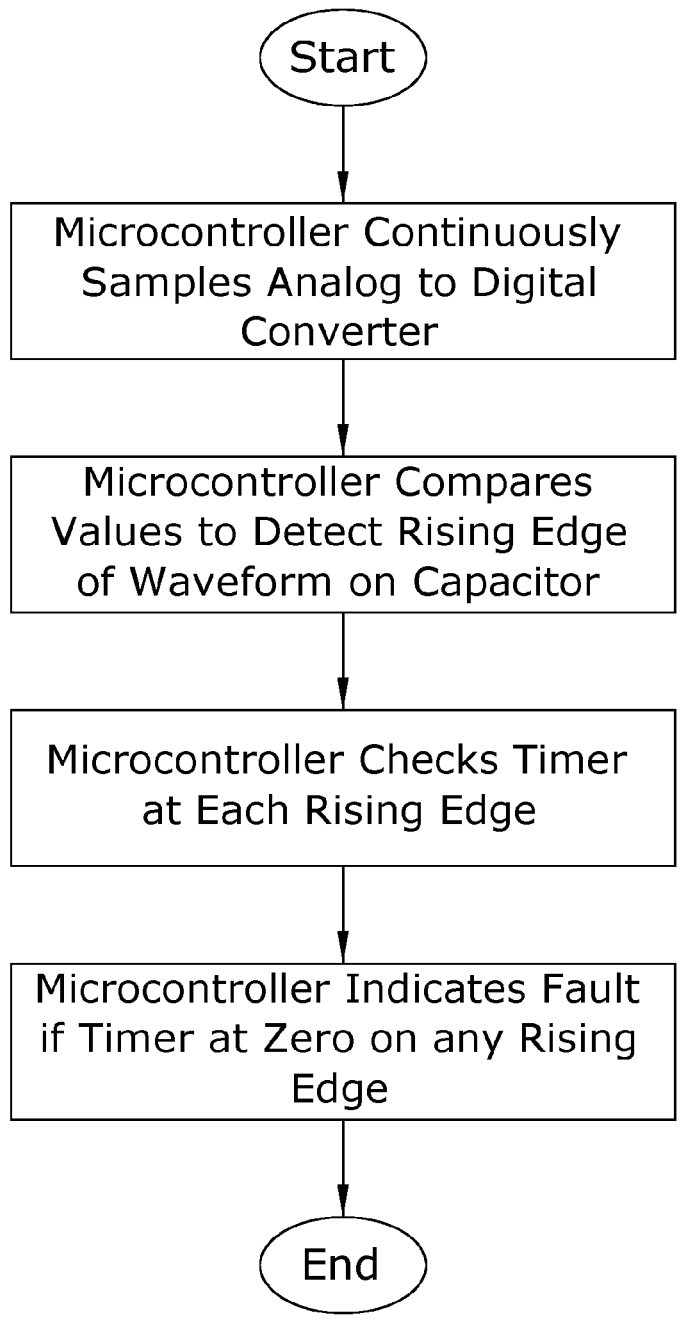
FIG. 13 is a flowchart illustrating an exemplary method for detecting faults in a tire defect tester using an analog-to-digital converter in combination with a microcontroller.

As discussed, the sensor 50 may comprise an analog-to-digital converter 52 or a comparator 62 in combination with the capacitor 40 and the microcontroller 60. FIG. 13 illustrates an exemplary method of detecting electrical discharges using an analog-to-digital converter 52. In this embodiment, the microcontroller 60 continuously samples the analog-to-digital converter 52. The sampling rate will preferably be significantly faster than the discharge rate of the capacitor 40 so that all discharges of the capacitor 40 are sampled and none are missed.

The conversion values of the analog-to-digital converter 52 are each compared to the preceding conversion value by the microcontroller 60. In this manner, the microcontroller 60 may detect the rising edge of the waveform on the discharge of the capacitor 40. When a rising edge is detected, the microcontroller 60 will check the value of the internal countdown timer that has been preset to an optimal threshold for rate of discharge of the probe 30.

By comparing each analog-to-digital conversion value to the previous value, the microcontroller 60 may detect the rising edge of the triangular voltage waveform on the capacitor 40. If this timer value is zero, the electrical discharge rate of the probe 30 has fallen below the rate threshold and the microcontroller 60 will thus find a fault in the tire defect tester 12. The fault may be indicated using the indicator 70. If the timer value is not zero, the electrical discharge rate of the probe 30 has not fallen below the rate threshold and the microcontroller 60 will not find a fault in the tire defect tester 12 and will thus continue with normal operation by resetting the countdown timer pending detection of a subsequent electrical discharge.

Figure 14:
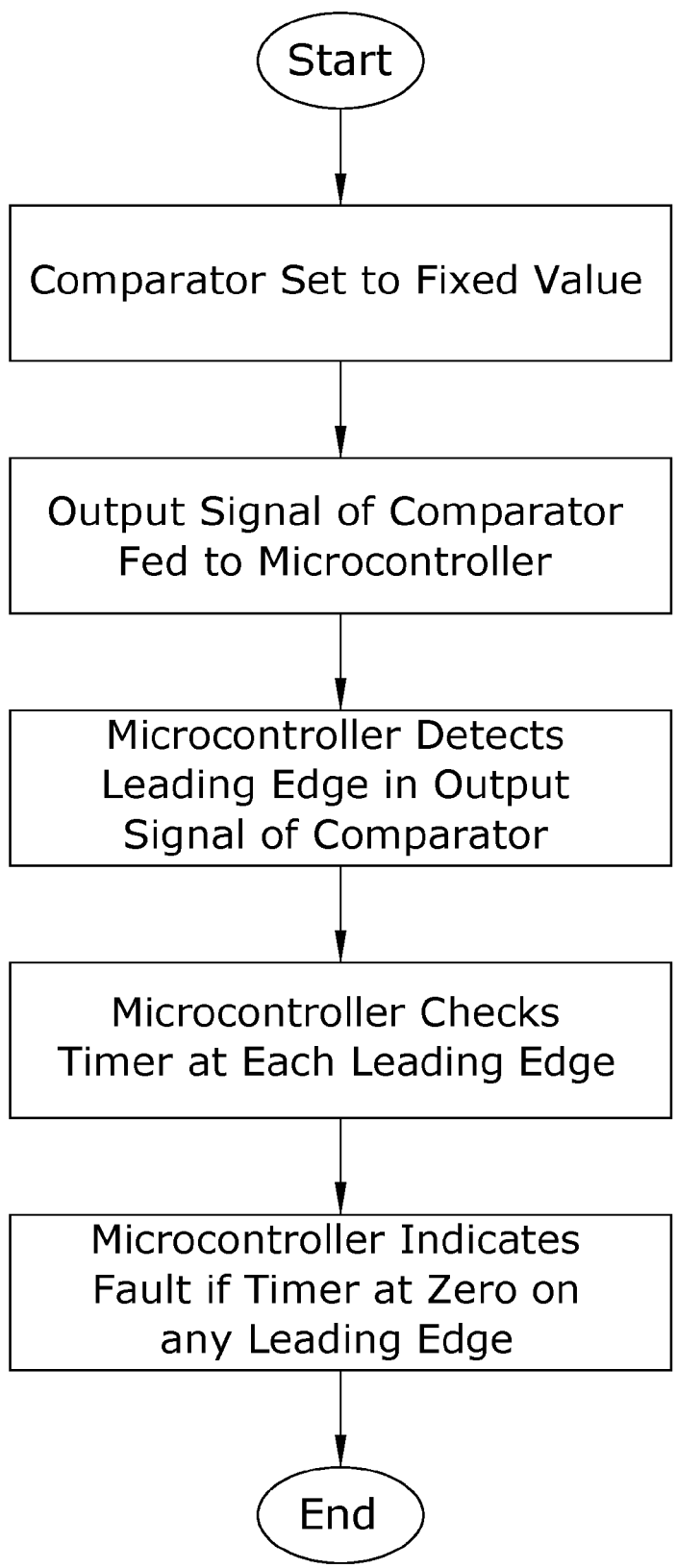
FIG. 14 is a flowchart illustrating an exemplary method for detecting faults in a tire defect tester using a comparator in combination with a microcontroller.

The sensor 50 may also comprise a comparator 62 in some embodiments. FIG. 14 illustrates an exemplary method which utilizes a comparator 62 in combination with the capacitor 40 and microcontroller 60 to detect discharges from the probe 30 and calculate a period of time between discharges. The comparator 62 is first set to a fixed value representing the minimum threshold rate of discharge for optimal performance of the tire defect tester 12.

The output signal of the comparator 62 is fed to the microcontroller 60, which will detect a leading edge in the output signal of the comparator 62. The countdown timer is checked each time a leading edge is detected; as such a leading edge from the comparator 62 is indication of a new electrical discharge from the probe 30. If the timer value is zero upon detection of a new leading edge from the comparator 62, the electrical discharge rate of the probe 30 has fallen below the rate threshold and the microcontroller 60 will thus find a fault in the tire defect tester 12. The fault may be indicated using the indicator 70. If the timer value is not zero, the electrical discharge rate of the probe 30 has not fallen below the rate threshold and the microcontroller 60 will not find a fault in the tire defect tester 12 and will thus continue with normal operation by resetting the countdown timer pending detection of a subsequent electrical discharge.

Unless otherwise defined, all technical and scientific terms used herein have the same meaning as commonly understood by one of ordinary skill in the art to which this invention belongs. Although methods and materials similar to or equivalent to those described herein can be used in the practice or testing of the electrical discharge testing system, suitable methods and materials are described above. All publications, patent applications, patents, and other references mentioned herein are incorporated by reference in their entirety to the extent allowed by applicable law and regulations. The electrical discharge testing system may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. An electrical discharge testing system for a tire defect tester, comprising:
   a tire defect tester comprising a probe adapted to periodically discharge electricity;
   a sensor for detecting the discharge of the probe, wherein the sensor is adapted to detect when a period of time between discharges of the probe exceeds a threshold;
   a transformer including a primary coil and a secondary coil, wherein the probe is connected to the primary coil and the sensor is connected to the secondary coil;
   a capacitor connected to the secondary coil of the transformer such that the capacitor is charged when a current pulses through the secondary coil of the transformer; and
   an indicator adapted to provide an indication when the period of time between discharges of the probe exceeds the threshold;
   wherein the sensor is adapted to detect each discharge of the capacitor to determine the period of time between discharges of the probe.

2. The system of claim 1, further comprising a power supply connected to the probe through the primary coil of the transformer.

3. The system of claim 1, further comprising a microcontroller connected to the sensor for determining when the period of time between discharges of the probe exceeds the threshold.

4. The system of claim 3, further comprising an analog-to-digital converter connected to the discharge of the capacitor.

5. The system of claim 4, wherein the microcontroller is adapted to compare values from the analog-to-digital converter to determine the period of time between discharges of the probe.

6. The system of claim 3, further comprising a comparator connected to the discharge of the capacitor.

7. The system of claim 6, wherein the microcontroller is adapted to receive periodic outputs from the comparator to determine the period of time between discharges of the probe.

8. A method of detecting an electrical discharge fault in a tire defect tester, comprising:
   providing a tire defect tester comprising a probe, a sensor, and a microcontroller, wherein the probe and the sensor are each electrically connected to a capacitor;
   periodically electrically discharging the probe to test for defects in a tire;
   setting an optimal period of time between electrical discharges of the probe by the microcontroller;
   detecting a first electrical discharge from the capacitor by a sensor;
   detecting a second electrical discharge from the capacitor by the sensor;
   calculating a period of time between the first electrical discharge of the capacitor and the second electrical discharge of the capacitor by the microcontroller;
   indicating a fault by the microcontroller if the period of time between the first electrical discharge of the capacitor and the second electrical discharge of the capacitor exceeds the optimal period of time; and
   not indicating the fault by the microcontroller if the period of time between the first electrical discharge of the capacitor and the second electrical discharge of the capacitor is equal to or less than the optimal period of time.

9. The method of claim 8, further comprising the step of connecting the probe to a primary coil of a transformer.

10. The method of claim 9, further comprising the step of connecting a capacitor to the secondary coil of the transformer.

11. The method of claim 10, wherein a first current pulse is created across the secondary coil of the capacitor upon the first electrical discharge from the probe and a second current pulse is created across the secondary coil of the capacitor upon the second electrical discharge from the probe.

12. The method of claim 11, further comprising the step of detecting the first current pulse by the sensor to indicate the first electrical discharge from the probe and detecting the second current pulse by the sensor to indicate the second electrical discharge from the probe.

13. The method of claim 8, further comprising the step of counting down a timer from a threshold value upon detection of the first electrical discharge.

14. The method of claim 13, further comprising the step of checking the timer upon detection of the second electrical discharge by the sensor.

15. The method of claim 14, further comprising the steps of indicating a fault if the timer is zero upon detection of the second electrical discharge by the sensor and not indicating a fault if the timer is not zero upon detection of the second electrical discharge by the sensor.

* * * * *